(12) United States Patent
Carter et al.

(10) Patent No.: US 8,165,892 B2
(45) Date of Patent: Apr. 24, 2012

(54) MONITORING DRUG PACKAGING IN CLINICAL TRIAL PROCESS

(75) Inventors: Paul Laurence Carter, Harlow (GB); Stephen Day, Harlow (GB); Peter Graham Evans, Harlow (GB); Lesley Julia George, Harlow (GB)

(73) Assignee: SmithKline Beeacham P.L.C., Brentford, Middlesex (GB)

( * ) Notice: Subject to any disclaimer, the term of this patent is extended or adjusted under 35 U.S.C. 154(b) by 1551 days.

(21) Appl. No.: 10/481,219

(22) PCT Filed: Jun. 21, 2002

(86) PCT No.: PCT/EP02/06895
§ 371 (c)(1),
(2), (4) Date: Jun. 14, 2004

(87) PCT Pub. No.: WO03/001429
PCT Pub. Date: Jan. 3, 2003

(65) Prior Publication Data
US 2004/0243620 A1    Dec. 2, 2004

(30) Foreign Application Priority Data

Jun. 23, 2001    (GB) .................................. 0115414.5

(51) Int. Cl.
*G06Q 10/00* (2012.01)
*G06Q 50/00* (2012.01)

(52) U.S. Cl. ............................................... 705/2; 705/3

(58) Field of Classification Search ................... 705/2–3
See application file for complete search history.

(56) References Cited

U.S. PATENT DOCUMENTS

| 4,857,716 | A | * | 8/1989 | Gombrich et al. ............. 235/375 |
| 5,208,762 | A | | 5/1993 | Charhut et al. |
| 5,845,255 | A | * | 12/1998 | Mayaud ............................ 705/3 |
| 5,907,493 | A | * | 5/1999 | Boyer et al. ................... 700/231 |
| 6,294,999 | B1 | * | 9/2001 | Yarin et al. .................. 340/573.1 |

FOREIGN PATENT DOCUMENTS

| GB | 2342203 |  | 4/2000 |
| GB | 2342203 | A * | 4/2000 |
| JP | 3060034 | U | 6/1991 |
| JP | 2000154673 | U | 6/2000 |
| WO | 0062221 |  | 10/2000 |

* cited by examiner

*Primary Examiner* — Sheetal R Rangrej
(74) *Attorney, Agent, or Firm* — James P. Riek

(57) ABSTRACT

A method for automatically tracking compliance in a clinical trials process involving one or more operations comprising selecting a container; associating an identifier with the container, the identifier having a unique signature data item thereon; reading the unique signature data item to a relational database; performing a first operation relating to the container; checking the performance of the first operation against a compliance standard; following the successful completion of the first operation, writing an associated compliance data item to the relational database; optionally performing one or more further operations relating to the container; and following the successful completion of each optional further operation or a package thereof, writing an associated compliance data item to the database.

17 Claims, 8 Drawing Sheets

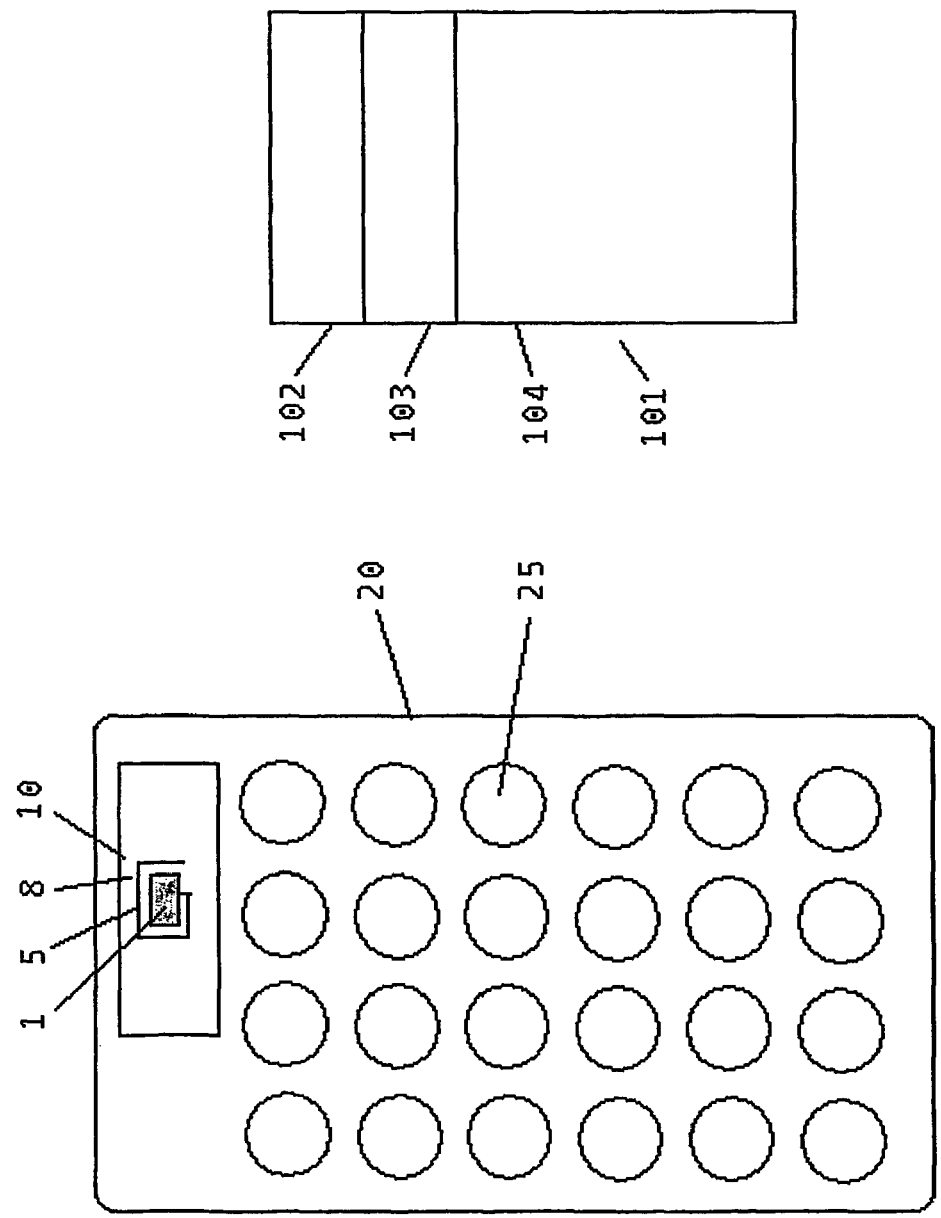

230 Select Container
↓
231 Associate Tag With Container
↓
232 Read Signature data item on tag to Database
↓
233 Operation 1
↓
234 Check performance against compliance standard
↓
235 Write Compliance Data Item on DB if Operation 1 Successful
↓
236 Read Tag
↓
237 Check associated compliance data item on DB
↓
238 If Compliance Data Item
↓                    ↓
239 Present        240 Absent ———→ 241 Reject
↓
242 Operation 2
↓
243 Write Compliance Data Item on DB if Operation 2 Successful
↓
244 Final Operation
↓
245 Write Compliance Data Item on DB if Final Operation Successful
↓
246 Read for Final Compliance Check
↓                    ↓
247 If Final Check   248 If Final Check —→249 Reject
    Successful          Unsuccessful
↓
250 Generate Final Data Compliance Item
↓
251 Clinical Trial Process Complete

Fig. 3

MONITORING DRUG PACKAGING IN CLINICAL TRIAL PROCESS

RELATED APPLICATIONS

This application is filed pursuant to 35 USC 371 as a United States National Phase Application of International Patent Application Serial No. PCT/EP02/06895 filed Jun. 21, 2002, which claims priority from GB0115414.5 filed on Jun. 23, 2001 in the United Kingdom.

BACKGROUND

Description of the Related Art

The invention relates to a method of automatically tracking compliance in a clinical trial process.

A clinical trial is the testing of a medicament or drug entity in humans in order to determine its efficacy and safety. Most clinical trials require the drug entity to be administered to volunteers or patients, the trial also requiring that both placebo, where no medicament is present, and a known 'standard' or 'comparator' medicament (typically a product from a competitive pharmaceutical company), are administered to volunteers or patients within the study. Thus a patient or volunteer can be treated with the drug entity, placebo and/or comparator in any combination depending upon the design of the study.

Such trials are complex in nature, the degree of complexity depending upon the level of trial involved. Trials can be divided into four Phases, as described below:

Phase I: small studies, typically involving volunteers who are aware of the content of each individual pack or container (i.e. an 'open study') and which may only require one bottle of medication. Alternatively, the study may be 'blinded' and the volunteer unaware of the nature of their treatment regime.

Phase II: larger studies involving up to several hundred patients or subjects, typically used to determine the optimum dose for a new drug. The study may incorporate the use of placebo and comparator treatments and may be 'open' or 'blinded'. The number of bottles involved in such studies may be in the region of hundreds to several thousand.

Phase III: larger studies, used to demonstrate the efficacy of the new drug, conducted in patient groups ranging from hundreds to several thousand in total. These studies will often include placebo and comparator treatments and will usually be 'blinded' in design. The duration of the study may vary from a few days to several years, involving from several hundred to hundreds of thousands of drug containers.

Phase IV: post marketing-studies: these studies vary in size and complexity, may be open or blinded and may or may not include comparators. The size and complexity of these studies are similar to those for a phase II study.

The clinical trial process encompasses a range of different and complex operations. For example, in a simplified format, it would involve the production of the investigational or candidate drug (i.e. synthesis and formulation of the active ingredient or chemical entity), packaging, labelling and dispatch to Investigator Sites, administration to patients/volunteers, physician assessments and return of biological samples (e.g. blood, urine samples) for analysis by Metabolism and Pharmacokinetic Groups.

Furthermore, the manufacture, packaging and administration/use of drugs is subject to regulatory control. Thus, for example, the packaging of drug candidates or 'investigational products' used in clinical trials is subject to the same regulatory control as is the packaging of any other pharmaceutical products. For example, in Europe, the EC guide to Good Manufacturing Practice (1997) must be followed, while the US Code of Federal Regulations. 21—Food and Drugs (Part 11—Electronic Records; Part 210—Current Good Manufacturing Practice in Manufacturing, Processing, Packaging or Holding Drugs; Part 211—Current Good Manufacturing Practice for Finished Pharmaceuticals) must be adhered to in the USA. Of particular relevance are Annex 13 of the EC guide to Good Manufacturing Practice 'Manufacture of Investigational Medicinal Products' and the US 'Guideline on the Preparation of Investigational New Drug Products'. There are additional regulatory requirements for the labels used for drug candidates; again these requirements will vary for each country participating in the clinical trial.

The design and information content of labels for clinical trials, particularly blinded studies, is such as to give no indication as to the identity of the drug to the patient and thus prevent bias of the study. This presents problems in traceability of the containers, where minimal details are presented on the label (such as dosage regime and patient number). Difficulties may also arise for all those involved in the manufacture, packaging and storage of the containers in trying to identify drug details, such as chemical identity and batch number that are often in coded format. The system is prone to errors, for example through mislabelling of containers that may arise during packaging and/or distribution and thus invalidate the study, and errors may occur at other stages in even the best managed system. While stringent controls have been put in place within the pharmaceutical industry to prevent such mislabelling, these controls require additional checks and are extremely resource intensive in terms of manpower and time.

Errors may also arise once the drug containers reach Investigator Sites where clinicians will give each patient or volunteer their specific medicament regime for the course of the study. The wrong container (or pack containing several drugs) may be inadvertently given to a patient, who will then unknowingly take a different medicament regime over the course of the study. There is therefore a need to provide clinicians/physicians with the means to rapidly read and interpret the information on each container and thus verify their contents without having to undergo the lengthy process of consulting the pharmacy directly. Such means would enable the clinicians to 'break the blind' and determine the patient's medicament regime instantly.

It is not uncommon in clinical trial studies for biological samples, such as blood or urine, to be taken from patients at Investigator Sites for return to the laboratory for analysis by a metabolism or pharmacokinetics group. Once again, errors may arise during this process if containers are incorrectly labelled by the site. For accurate study data the link between medication, patient and samples must be maintained.

For these reasons, there is a fundamental requirement for the ability to identify and track individual containers of investigational drugs as they progress throughout the clinical trial process. This ability enables pharmaceutical companies to meet regulatory requirements, in the form of providing comprehensive data packages or audits and also allows 'product recall' for analysis, if necessary. Product recall may be necessary in the event of adverse or unusual patient reaction to the drug or to confirm drug integrity and concentration throughout the clinical trial. Pharmaceutical companies currently take painstaking efforts to check and control labelling of drug containers and dispatch to Investigator Sites by checking and double checking label information. This process is time consuming, expensive and can be prone to errors.

It is an objective of the present invention to provide a method for validating that specific operations have been completed to meet defined criteria and thus to assure quality compliance throughout the process. It is a further object of the present invention to provide a method for identifying and tracking such containers throughout the clinical trial process and to maintain a full electronic data record of each container by which a complete audit trail can be produced. It is a further objective of the present invention to provide a means for selecting specific containers for use in the clinical trial process and for ensuring that these containers are correctly labelled following predetermined operations.

WO-A-98/09598 describes an automated packaging line for filling bottles with different pharmaceutical solid dosage forms (such as tablets) and for providing customised labelling for each bottle. The packaging line incorporates the use of an intelligent data-carrying puck to carry each bottle together with a puck-handling system to ensure that the bottles have been filled correctly.

GB-A-2342203 provides a method for packaging a drug in a container having a remote-readable identifier attached thereto. The drug details are stored on a database, and printed onto a label for application to the container.

SUMMARY OF THE INVENTION

According to one aspect of the present invention there is provided a method for automatically tracking compliance in a clinical trial process involving one or more operations comprising:
  selecting a container;
  associating an identifier with the container, the identifier having a unique signature data item thereon;
  reading the unique signature data item to a relational database;
  performing a first operation relating to the container;
  checking the performance of the operation against a compliance standard;
  following the successful completion of the first operation, writing an associated compliance data item to the relational database;
  optionally performing one or more further operations relating to the container; and,
following the successful completion of each optional further operation or a package thereof, writing an associated compliance data item on the relational database.

According to another aspect of the present invention there is provided a method for automatically tracking compliance, comprising a part of a clinical trial process involving one or more operations involving one or more container used in said operation, comprising:
  selecting a container;
  associating an identifier with the container, the identifier having a unique signature data item thereon;
  reading the unique signature data item to a relational database;
  performing a first operation relating to the container;
  checking the performance of the operation against a compliance standard;
  following the successful completion of the first operation, writing an associated compliance data item to the relational database;
  optionally performing one or more further operations relating to the container;
  and;
following the successful completion of each optional further operation or a package thereof, writing an associated compliance data item on the relational database.

The clinical trial process may be any of a Phase I, II, III or IV study as described above. The method of the invention may be applied to one, more than one or all of the operations which make up a clinical trial process.

The first and optional further operation may be any operation used in a clinical trial process, and the compliance standard may be appropriate to the operation. Typical non-limiting examples of operations involved in a clinical trial process and corresponding associated compliance standards relevant thereto, and in relation to which the present invention may be used, include:

The use of one or more suitable reagent, excipient and/or reaction conditions in the preparation and/or formulation of a drug substance; the associated compliance standard being confirming that such suitable reagents, excipients and/or reaction conditions have been used.

Selecting a container such as a vial or blister pack, and introducing the correct type, and quantity of a drug substance for trial, placebo or comparison drug substance into the container; the associated compliance standard being checking that the correct type, and/or quantity of a drug substance for trial, placebo or comparison drug substance has been introduced into the container. For example the quantity may comprise weight, volume or number of tablets.

Applying or removing a closure to or from a container, e.g. so that substances can be introduced into it; the associated compliance standard being checking whether or not the cap is in place.

Storing a container in a predetermined location, subsequently removing the container therefrom and optionally transferring it to another predetermined location; the associated compliance standard being confirming that the correct container is at the correct location.

Storing a container or substance under suitable environmental conditions such as temperature, humidity, or storage time; the associated compliance standard being to ensure that suitable environmental conditions have been followed.

Selecting a container such as a vial or blister pack and enclosing it in a secondary pack such as a carton; the associated compliance standard being checking that the correct container has been enclosed within the correct secondary pack.

Applying a label bearing information such as reference alphanumeric data or a destination address, to a container such as a vial or blister pack or a secondary container; the associated compliance standard being checking that the correct label has been applied to the container.

Dispatching to or receiving a container at a predetermined address; the associated compliance standard being checking that the address is correct and/or that the correct container has arrived at the correct address.

Dispensing a container of a substance to a patient participating in a clinical trial; the associated compliance standard being checking that the correct container has been dispensed, and/or that the correct patient has received the container.

Transmitting and receiving information relating to the container, e.g. relating to its contents e.g. clinical trial data, to a predetermined recipient; the associated compliance standard being ensuring that the correct information is sent to and received by the correct recipient.

With any operation, e.g. the above-mentioned operations an associated compliance standard may also be a confirmation that the correct person(s), e.g. in terms of identity and/or responsibility, have performed the operation.

The term 'automatically' is used to mean non-manual, i.e. without manual intervention. In particular, reading and generating (e.g. writing) steps herein are conducted automatically. However the term "automatic" as used herein may include a process in which one or more operations are performed manually in addition to one or more operation being performed automatically, or may be entirely automatic.

A relational database may take the form of an electronic data management system.

The unique signature data item may comprise a unique machine readable number or code. In practical applications, it is anticipated that each identifier may be uniquely assigned a signature data item on manufacture, and that unique batches of signatures may be acquired from the manufacturer of the identifier, typically under exclusive contract terms. Alternatively, the unique signature data item may be written on to the identifier by the user. The unique signature data item may comprise compliance data, but in most applications this will be stored as a separate compliance data item.

The term "compliance data item" as used herein may include writing to the relational database an acknowledgement that the compliance standard relating to the operation has been successfully complied with. Failure to comply with the compliance standard may also be written to the relational database as a negative compliance data item, or the absence of the compliance data item may be interpreted as a negative compliance data item.

Preferably, the method additionally comprises reading the associated compliance data item and acknowledging confirmation of the reading prior to performing any further operation relating to the container.

The identifier may have a memory and the method may additionally comprise writing the compliance data item to the memory of the identifier. This may comprise writing both the nature of the compliance data item and compliance therewith.

Preferably, the method additionally comprises reading at least one compliance data item in the identifier memory prior to performing further operations relating to the container.

In one aspect the method comprises checking the at least one compliance data item against a defined criterion stored on the relational database. The criterion may, for example, specify that the container has been filled with a drug, or that a label has been correctly affixed to the container, or compliance with any one or more of the abovementioned compliance standards.

Preferably, the at least one compliance data item is associated with the last performed operation or a plurality of operations on the relational database.

Preferably, non-compliance with any compliance standard results in the abandonment of the clinical trial process for the container and in the rejection of the container.

Preferably, the method additionally comprises a final reading step involving reading all compliance data items on the relational database and/or the identifier memory subsequent to the completion of the clinical trial operations. More preferably, the method additionally comprises checking all compliance data items against defined full compliance criteria on the relational database.

Preferably, full compliance with the check results in the generation of a full compliance data item on the relational database and/or writing a full compliance data item to the memory of the identifier.

The method of the invention may be performed in various ways, but for example two distinct variations of the compliance checking process can be envisaged.

In the first variation, the compliance data item comprises an operation or list of operations (possibly preloaded into the memory of the relational database) which must be carried out for full compliance to be registered. The subsequent checking then involves 'ticking off' the compliance data item (by writing to the database or identifier memory) associated with any operation once it has been completed. The 'ticking off' would be confirmed by a competent checker thus enabling electronic data records with full electronic signature to be maintained. This variation is akin to a 'ticking the box' process.

In the second variation, a positive compliance data item for each operation is written to the database (and optionally the identifier memory) following the completion thereof. As the method progresses a positive listing of completed actions is written to the database and the identifier memory. This variation is thus akin to a 'completed actions listing' process.

The process of the invention may comprise either or both of such variations, e.g. applied separately to respective different operations.

The first operation may be carried out at a first site and at least one of the one or more further operations may be carried out at the same site, or a second or further site. For example a first site may be a site from which a container of a drug or other substance for use in a clinical trial is dispatched, and a second site may be a clinic at which the container is received and dispensed therefrom to one or more patient participating in the trial. In this latter situation the compliance standard may comprise the clinic confirming back to the first site that the container has been received, and/or applying a label at the clinic and confirming that the correct label has been applied. The site may be at the same or a different geographical location (e.g. within different areas of the same pharmaceutical plant or in entirely different locations). Preferably, the first site and the one or more further sites are linked via a network computer system to enable transfer of data therebetween to the relational database.

Preferably, writing to the memory is by wireless data transfer thereto. More preferably, reading of the database or the memory is by wireless data transfer therefrom.

Wireless data transfer may be by data transfer means selected from the group consisting of capacitative data transfer means, transformative coupling data transfer means, electrical data transfer means and magnetic data transfer means.

Capacitative data transfer involves the transfer of data from a reader/writer from the identifier in the form of high energy alternating current, when the reader/writer and identifier are in close proximity. These data are transferred by the reader/writer to the database memory for storage thereon. Similarly, data can be transferred from the database memory to the identifier memory by the reader/writer.

Transformer coupling data transfer involves transfer of data from the primary winding on a reader/writer to a secondary winding on the identifier. The transformer supplies power to the identifier as well as information that can be written or read from the identifier with an appropriate reader/writer. Data can be stored on the memory on the identifier as well as being written to the relational database.

An alternative form of electrical data transfer is by direct physical contact of, for example, two brushes, one of which contains an electrical signal. Power is supplied to the identifier to effect data transfer to write/read information from the memory using an appropriate writer/reader.

Magnetic data transfer is effected by the generation of a suitable magnetic field by, for example, inductive means. Energy is provided to effect data transfer to write/read information from the memory using a suitable reader/writer.

Data may also be transferred to/from the identifier by optical data transfer means. Visible or infra red light energy can be transmitted from a light emitting diode, acting as a writer, to a photo electric diode on the identifier. The photo electric diode can then translate the information contained in the signal into electrical form which can be transferred and recorded on the memory. Information retrieval from the chip memory involves a light emitting diode on the identifier transmitting a signal back to a reader/writer. A suitable standard method for two communication over an infrared link is "IrDA".

Data transfer may also be effected by radiofrequency data transfer means. Information is transmitted from a radiofrequency writer to an antenna on the identifier and transferred for storage to a memory. Data can be read from the chip by a suitable reader which transmits radiofrequency energy to the identifier, thereby energising the identifier to enable data transfer.

Suitably, the identifier additionally comprises an antenna for transmitting or receiving energy in e.g. optical, electrical or magnetic form.

The identifier may be a radiofrequency identifier comprising an antenna for transmitting or receiving radiofrequency energy, and an integrated circuit chip connecting with said antenna, said chip comprising the memory. Radiofrequency identifiers are also known which lack a memory chip.

The radiofrequency identifier can be any known radiofrequency identifier. Such identifiers are sometimes known as radiofrequency transponders or radiofrequency identification (RFID) tags. Suitable radiofrequency identifiers include those sold by Phillips Semiconductors of the Netherlands under the trade marks Hitag, and Icode those sold by Amtech Systems Corporation of the United States of America under the trade mark Intellitag, and those sold by Texas Instruments of the United States of America under the trade mark Tagit.

Preferably, the antenna is capable of transmitting or receiving radiofrequency energy having a frequency of from 100 KHz to 2.5 GHz. More preferably, the antenna is adapted to transmit or receive radiofrequency energy having a frequency selected from the group consisting of 125 KHz, 13.56 MHz and 2.4 GHz. Higher frequencies are preferred because the distance between the reader/writer and the identifier may be increased.

The RFID tags herein may be used in combination and/or integrated with other traditional product labelling methods including visual text, machine-readable text, bar codes and dot codes.

The identifier may be connected to the container by any suitable means, such as adhesive label or being moulded into the container body. Suitable containers include primary containers such as bottles, vials, blister packs and ampoules.

The operation may comprise selecting the second or further container having an identifier associated thereto, the identifier having a unique signature data item; reading the unique signature data item to the relational database; performing one or more operations relating to the first, second or further container; checking the performance of the one or more operations against a compliance standard; and following the successful completion of each operation or a package thereof, generating an associated compliance data item on the relational database.

Preferably, the identifier has a memory and the method additionally comprises writing the compliance data item to the identifier memory.

The application of the method of the invention to various operations, one or more of which may be performed in a clinical trials process will now be described in more detail.

For example the operation may comprise preparing a label comprising textual information and attaching the label to a first, second or further container (such as a vial, bottle or blister pack, or a carton containing one or more of these); the method comprising selecting the first, second or further container by reading the unique signature data item associated therewith; preparing the label; attaching the label to the container; confirming that the label is attached to the container; and writing an associated compliance data item on the relational database.

For example the immediately above-mentioned operation may comprise preparing a label comprising textual information and also an identifier comprising a unique signature data item, and confirming that the label is attached to the container may be done by reading the unique signature data items attached to both the container and the label.

GB-A-2342203 describes a method for packaging a drug in containers having remote-readable identifiers affixed thereto wherein the identity of both the drug and the container are stored on a database and a label produced reproducing the labelling data associated with the identified container. However, there is no validation by a compliance check in this method that the label has been affixed to the correct container; errors may therefore arise due to mislabelling of containers.

The label may incorporate a unique signature data item comprising machine-readable information such as a bar code, and the operation may involve reading the bar code and relating the information therein with the unique signature data item in the relational database. Preferably, the label identifier has a memory, the method additionally comprising writing the compliance data item to the identifier memory on the container and/or the label.

For example the operation may be a filling operation involving filling any of the containers with a pre-defined quantity of a chemical or of a dosage unit. Preferably, the chemical is selected from the group consisting of active ingredient, excipient, formulant, stabiliser, formulated drug candidate, medicament and placebo. A dosage unit may, for example, be in the form of a tablet or capsule. Compliance criteria may, for example, be the quantity of chemical or dosage units added, their active shelf-life and/or environmental conditions to which they have been exposed.

For example the operation may be a formulation operation involving formulating an active ingredient with one or more excipients. Compliance standards may, for example, be the quantity of excipient and/or the reaction conditions of the formulation operation (e.g. duration, temperature, pressure etc.).

For example the operation may be an assembly operation comprising assembly of a patient pack, i.e. for dispatch to a patient participating in the clinical trial, with one or more containers, the containers being positioned at pre-defined positions within the pack. The system is capable of confirming both that the containers have been positioned at the correct positions within the pack and that the correct containers have been packed.

Such an operation may comprise selecting the container by reading the unique signature data item associated therewith; reading the data compliance item on the relational database or in the identifier memory; placing the container in a second container (such as a carton) suitable for dispatch; and following the successful completion of the operation writing a compliance data item on the relational database. The container may, for example, be a bottle, blister pack or patient pack. Compliance standards may, for example, include ensuring that each container is correctly labelled and positioned within the second container and that this container is subsequently sealed and ready for dispatch.

Preferably, the method additionally comprises writing the compliance data item to the identifier memory.

Preferably, the method additionally comprises writing a label for the carton on checking that the data compliance item is present. Information regarding dispatch address/contents of the carton etc. will be taken from the relational database and written on the label.

For example the operation may comprise dispatch of the container to or from a clinical trial investigator site. Typically dispatch would be from the Clinical Supplies Packaging unit of a pharmaceutical company. Preferably, the dispatch of the carton is confirmed by writing a compliance data item on the relational database.

For example the method may additionally comprise writing environmental data from a sensor associated with the a transport and/or storage container/facility throughout transport and storage of the container to the identifier memory. The sensor may be located in a transport container or carrier, such as a road, shipping or air freight carrier, which is capable of transmitting environmental data to the memory at pre-defined time points. The environmental data may, for example, be temperature, pressure, humidity or light data. These data can then be transmitted to the relational database at pre-defined time points, such as delivery of the dispatch and the end of storage. In this way, it is possible to record the environmental extremes to which the containers have been exposed and to reject any containers which have been exposed to conditions outside pre-defined limits (e.g. minimum/maximum temperatures for a specific container/drug). Such pre-defined limits would take the form of compliance standards on the relational database.

For example receipt of the carton at the Investigator Site may be confirmed by reading the unique signature data item and transmitting a compliance data item recording safe receipt to the relational database. The identifier is read by any suitable reader/writer which can transmit information, either directly or indirectly, to the database.

For example such a compliance data item may be transmitted to the relational database via a public or private access network computer system. The internet is one suitable example of a public access network computer system. For example the method of the invention may comprise communicating with a user-specific network address in the network computer system. Preferably the user-specific address is selected from the group consisting of a web site address, an e-mail address and a file protocol address.

The method may comprise confining receipt of a clinical trial container by a patient, the patient having an identifier with a unique signature data item associated thereto, the patient identity being stored on the relational database in association with the unique signature data item, by reading both the container and the patient signature item and cross-checking on the relational database. Thus, the clinician or physician at the Investigator Site will give patients involved in the clinical trial their individual medicament regimes, either in the form of specific patient packs or labelled containers. Each patient will already have been allocated a particular medicament regime which is stored on the relational database prior to the preparation of the containers/patient packs, as discussed above. The use of patient identifiers forms another safeguard and compliance check to ensure that patients/volunteers obtain the correct medicament regime at the outset of the trial. The patient identifiers can also form an important link in facilitating a complete electronic audit trail for each clinical trial sample/drug product. Patient identifiers may comprise a 'Smart Card' having a memory wherein the patient's details, such as name, age, sex, weight, medical history and medicament regime, are stored. Alternatively, the identifier may only comprise the unique signature item, all other details being stored centrally on the relational database.

The method may comprise returning a biological sample taken from the patient for analysis, the method comprising associating an identifier with a container, the identifier comprising a unique signature data item; placing the biological sample within the container; reading the unique signature data item, reading the patient identifier; and writing a data compliance item associating the container and the patient unique signature data items on the relational database.

Thus the signature data item or compliance data item can be used to check compliance throughout the clinical trial process, ranging from checking material status and availability to ensuring that containers have been correctly labelled. Compliance may thus be tracked automatically using the unique signature item and/or compliance data items by checking, for example, any of the following factors:

the correct container/pack/carton has been selected;
a filling/mixing/formulating operation has been successfully completed;
any activity is approved by a competent person;
training status of operator;
correct bulk and component materials are used in a process;
container correctly labelled;
container properly closed e.g. by a closure;
container positioning within a patient pack;
container dispatch/receipt at Investigator Site;
container receipt by patient.

The unique signature item and/or compliance data item can optionally be used to drive a pre-assigned process in the checklist. Thus, for example, the following tasks may be driven using these data items by means of links with the relational database:

print patient-specific details on a label in any language;
increment/decrement inventory;
logging environmental conditions;
links containers to patients.

A radiofrequency identifier ("RFID") may be on a carrier suitable for mounting to the container, or may be embedded in the material of the container such as a mouldable plastics material. Preferably, the carrier is a flexible label attachable to the container and not easily removed therefrom, or removable only to leave a visible indication. More preferably, the carrier is a rigid disc. More preferably, the carrier is a rectangular block.

The carrier may be mouldable to the container. Preferably, the carrier encases the identifier. Preferably, the carrier forms a hermetic seal for the identifier.

The carrier may comprise an insulating material. Preferably, the insulating material comprises a glass material, paper material or organic polymeric material such as polypropylene.

Alternatively, the carrier may comprise a ferrite material.

Preferably the identifier memory has plural memory areas thereon. The plural memory areas can be selected from a read only memory area, a write only memory area, a read/write memory area, a one time programmable memory area, a pre-set, non-amendable memory area and any mixtures thereof.

Preferably, any memory area contains data in encrypted form and/or is password protected.

Preferably, the reader is capable of reading multiple identifiers simultaneously by differentiating between individual identifiers within the same antenna field. The reader thus has 'anti-collision' capability.

The relational database may comprise a data memory, e.g. in a computer system, for storage of data; a microprocessor for performing operations on the data; and a signal output for outputting a signal relating to the data or the outcome of an operation on the data.

The relational database may be a distributed relational database comprising plural electronic data collectors, each comprising a data memory for storage of data; a microprocessor for performing operations on the data; and a signal output for outputting a signal relating to the data or the outcome of an operation on the data; wherein the plural electronic data collectors are in networked relationship to form the distributed relational database.

The electronic data collectors may comprise what are known in the art as 'field devices' which are used for local data collection. Each 'field device' may be capable of wireless communication to the other or to the relational database/electronic data management system.

A robotics system may form part of the relational database.

The method may additionally comprise communicating with a gateway to a network computer system to enable transfer of data between the network computer system and the relational database or any individual electronic data collectors thereof. More preferably, the method enables two-way transfer of data between the network computer system and the relational database.

The network computer system may comprise in embodiments, a local or wide area network, an intranet, an enterprise resource planning system or any similar network. Security features may be provided thereto including a firewall.

The communication (e.g. via a communicator) may be via radiofrequency or optical signals.

The communicator may communicate with the gateway via a second communications device. Preferably, the second communications device is a telecommunications device, more preferably a cellular phone or pager. Preferably, the communicator communicates with the second communications device using radiofrequency signals. A suitable (e.g. spread spectrum) protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

Preferably, the data are communicable between the network computer system and the relational database in encrypted form. All suitable methods of encryption or partial encryption are envisaged. Password protection may also be employed.

The network computer system comprises a public access network computer system. The internet is one suitable example of a public access network computer system, wherein the gateway can be any suitable gateway thereto including gateways managed by an internet service provider. The public access network computer system may also form part of a telecommunications system, which may itself be either a traditional copper wire system, a cellular system or an optical network.

The network computer system may comprise a private access network computer system and the gateway is a secure gateway. The private access network system may, for example, comprise an intranet or extranet which may, for example, be maintained by the pharmaceutical company. The secure gateway may for example include password protection; a firewall; and suitable encryption means.

The method preferably comprises communicating with a user-specific network address in the network computer system. More preferably, the user-specific network address is selected from the group consisting of a web-site address, an e-mail address and a file transfer protocol address.

In another aspect of the present invention there is provided a computer program comprising program means for, when executed on a computer, instructing the computer to control all of the steps of the invention as hereinbefore described.

In a further aspect of the present invention there is provided a computer program product comprising a computer readable recording medium having recorded thereon a computer program comprising code means for, when executed on a computer, instructing the computer to control the steps in a method for automatically tracking compliance in a clinical trials process involving successive operations of selecting a container; associating an identifier with the container, the identifier comprising a memory having a unique signature data item thereon; performing a first operation relating to the container; following the successful completion of said first operation, automatically generating an associated compliance data item on a relational database; performing one or more further operations relating to the container; and following the successful completion of each said further operation or any package thereof, generating an associated compliance data item on the relational database.

BRIEF DESCRIPTION OF THE DRAWINGS

The invention will now be described by way of example only with reference to the accompanying drawings, wherein:

FIG. 1b is a perspective view of a blister pack with a RFID tag attached thereto.

FIG. 2 is a schematic representation of the memory structure of an RFID tag.

FIG. 3 is a flow diagram of a method for tracking compliance in a clinical trial process.

DETAILED DESCRIPTION

Figure 1A:
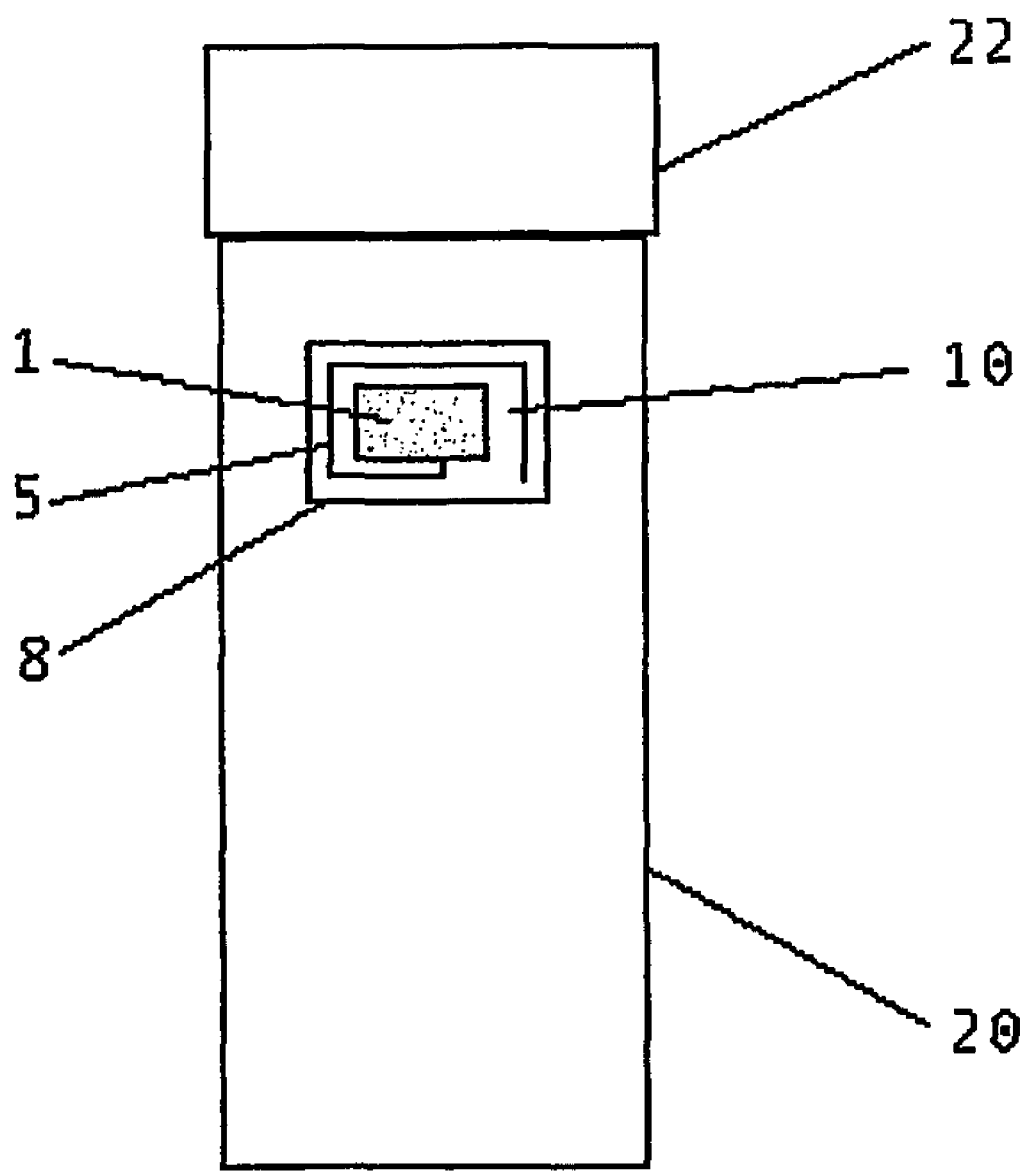
FIG. 1a is a perspective view of a container for a drug having a RFID tag attached thereto.

Referring to these figures, FIG. 1a shows RFID tag 10 attached to a container 20 for an investigator drug or medicament having a cap or lid 22. The RFID tag comprise an integrated circuit chip 1 connected to an antenna 5. The RFID tag illustrated is mounted on a flexible label 8 which is adhesively attached to container 20.

In alternative embodiments, it will be understood that the carrier may take several different forms, such as a rectangular label as illustrated, a rectangular block or a circular disc. The carrier may be affixed to the container by adhesion, hermetic or welding means. Alternatively the tag may be directly moulded into the body of the container (e.g. if made of a suitable plastic). All such are suitable for the method described herein.

In FIG. 1b the container 20 is in the form of a blister pack for packaging investigator drugs. The pack comprises a number of pockets 25 each containing a pharmaceutical dosage form. Blister packs are sealed after filling by an otherwise conventional burstable foil closure to provide protection from, for example, moisture and/or light.

FIG. 2 is a schematic representation of the memory structure of the RFID integrated circuit chip 101. Such chips are divided into unique blocks, typically numbering sixteen in total, with data being stored in non-volatile memory EEPROM, the EEPROM having a memory capacity of 512 bits with each block consisting of 4 bytes. However, for the sake of simplicity, in the illustration shown in FIG. 2 the tag is divided into three blocks 102-104 only.

The first block 102 contains a unique identifier such as a serial number, this information being in a read only format and being encoded on the chip at the time of manufacture such that this information cannot be altered once set. This unique identifier is a unique signature data item for the chip 101 and hence for the container 20 to which it is attached.

The second block 103 permits write access conditions to be determined for the third block 104, for example to allow read and write access to the remaining blocks. This block may be considered a 'secret area' in that access requires mutual authentication and enciphered data communications are used in this area. The second block 103 may be made read only once information has been written to it, i.e. it may become one time programmable.

The third block 104 can be considered to be a 'user' or 'public' area in that it may be programmed, by block two 103, such that information may be read from or written to it. This is generally the format in operation, information being read from and written to this area. Access can be password protected and data may be in encrypted format to enhance security.

In use, information from block one 102 (i.e. the unique serial number) will generally be used to identify the chip at each stage in a pre-determined process. Information will also be read from block three 104, to ensure that a given step in the operation has occurred. If satisfied that the operation has taken place successfully then additional information is written to block three 104, following the successful completion of the next stage in the process. Each step in the process is therefore validated and recorded by means of reading data on the chip and by transferring new information to it. These data can be stored electronically and the process monitored from a centralised data management system.

A flow diagram of a method for tracking compliance in a clinical trial process is shown in FIG. 3. The method begins by selecting 230 a first container having an RFID chip attached thereto by means of a label as described above, and associating 231 the RFID chip "tag" with it. The unique data signature item on the tag is then read 232 to the relational database (DB). A first operation 233 is carried out in relation to the container and checked 234 against a compliance standard. The compliance standard may, for example, define the filling weight or volume of a chemical to be added to the container. If the operation is successfully completed, a compliance data item is written 235 to the a relational database. The DB may form part of a data management system or be a central data base for the storage and retrieval of electronic data relating to a clinical trials program.

The RFID tag is subsequently read 236 by a radio frequency reader to identify the unique tag number and confirm 237 the presence of the associated data compliance item prior to conducting a further operation 242 on the container. At decision point 238, only if the compliance data item is present 239 will a further operation be carried out on the container 242, absence 240 of the data item resulting in discontinuance of the process and/or rejection of the container 241.

Following the successful completion of the second 242 and subsequent operations a compliance data item is written (Step 243) to the data base. These operations may, for example, comprise formulation, weighing, mixing, packaging, labelling, dispatch or receipt of the container. The operations may also involve the selection, validation and further processing of one or more further RFID tagged containers used in the clinical trial process.

On completion of the final operation 244 in the clinical trial process a final compliance data item is written 245 to the database. This compliance data item is read 246 and checked 247-248 against defined full compliance criteria on the relational database. If the final check is unsuccessful 248 then the container is rejected or recalled 249; however, if the final check is satisfactory 247 then a summary data compliance item is generated on the database 250 to signify that the clinical trial process for that container has been completed 251.

Figure 4:
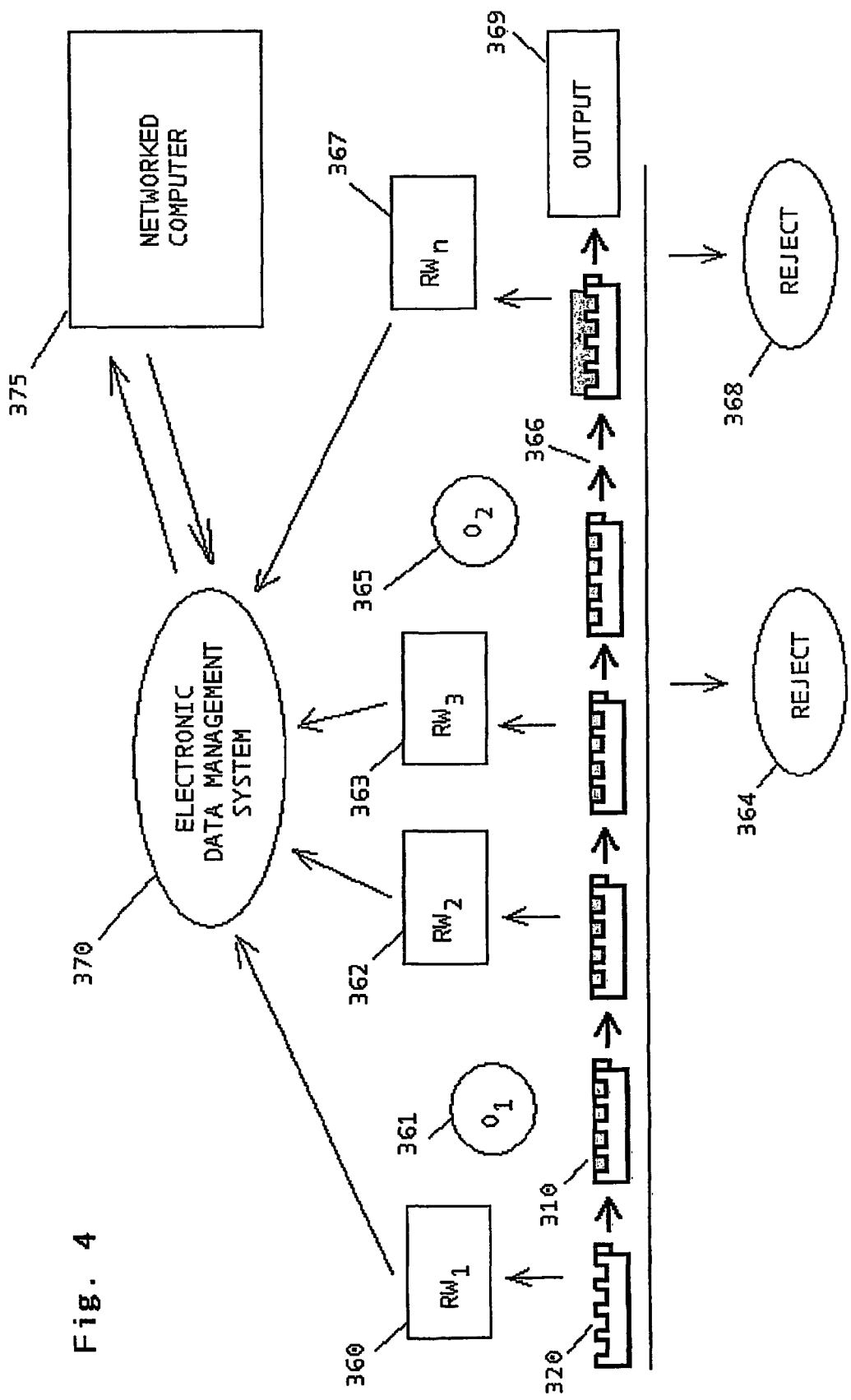
FIG. 4 is a schematic diagram of a system employing a method for tracking compliance in a clinical trial process.

A schematic representation of a system employing a method for tracking compliance in a clinical trial process is shown in FIG. 4. The diagram illustrates a simplified process for filling a blister pack 320 with an investigator drug and sealing the pack on addition of the drug.

An RFID tag 310 is associated with an empty blister pack 320 and the unique signature data item read from the tag and written 360 to a relational database (or electronic data management system) 370 by Reader/Writer RW1. The first operation O1 is then carried out 361, such as filling the pockets of the pack with an investigator drug. After checking against a compliance standard that the operation has been successfully carried out, a data compliance item is written 362 to the electronic data management system 370 by Reader/Writer RW2. This information is validated at 363 when Reader/Writer R3 reads the unique data signature on the tag; the unique code is then cross-checked against the respective data compliance item on the electronic data management system 370. If the information is absent then the blister pack is rejected 364; if present then the next operation O2, for example attaching a label to the blister pack 320, is performed 365.

The process is repeated 366 in connection with further operations, e.g. checking that the correct label has been applied to the blister pack 320, or that the blister pack 320 has been put in the correct secondary pack such as a carton, at the same or different sites which may, or may not, be distant from the first site, until Reader/Writer RWn validates 367 the entire process in a final compliance check. If the system is not satisfied that all of the operations have been successfully carried out then the blister pack is rejected 368. At any point of automation failure, the stage of each blister pack in the process is known. If validation is successful then the process is deemed complete and the blister pack is considered a final product or output 369 and is ready for dispatch to a Clinical Investigator Site.

In the diagram the process is controlled by an electronic data management system 370 which is capable of receiving and sending information to the chip via the Reader/Writers RW. Two way communication is therefore possible between the data management system 370 and the RFID tag 310. Thus, for example, data compliance items may additionally be written to the chip memory (not shown) as well as to the electronic data management system 370.

The electronic data management system may form part of a robotics system (not shown). The system may also be connected to a networked computer system 375 to allow transfer of data between both systems, preferably these data being in an encrypted format. The networked computer system may be a publicly accessible system, such as the internet, or a privately accessible system such as an intranet or extranet.

FIGS. 5a-d are a schematic representation of a method of selecting and labelling containers in a clinical trials process.

Figure 5B:
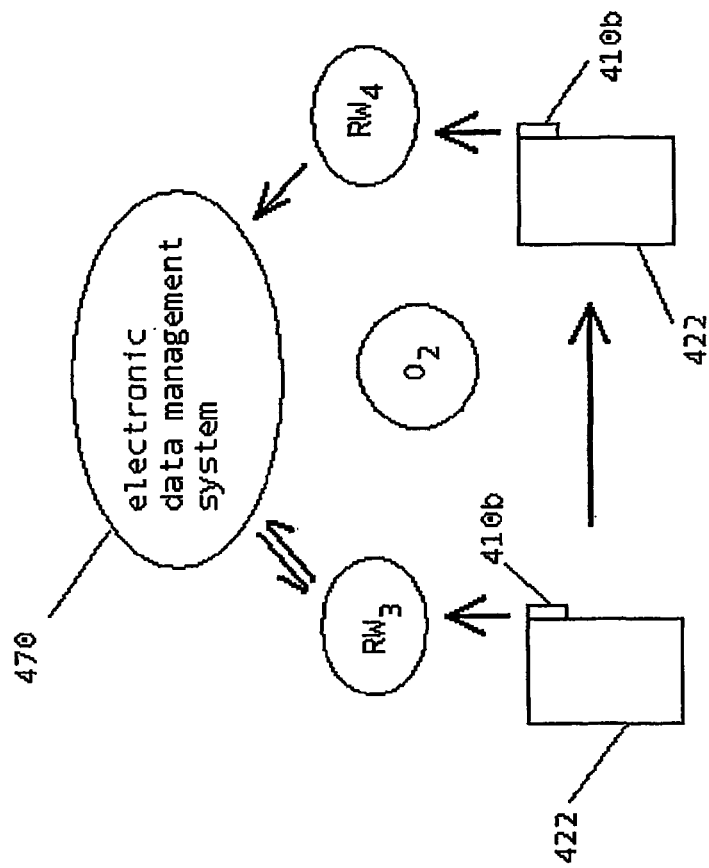
FIGS. 5a & b depict a method for selecting a first and a second container.
FIG. 5c shows a method for transferring a drug from the first container of FIG. 5a to the second container of FIG. 5b.
FIG. 5d illustrates a method of validating attachment of a label to a container.
FIG. 5e illustrates an alternative method of validating attachment of a label to a container.
Figure 5A:
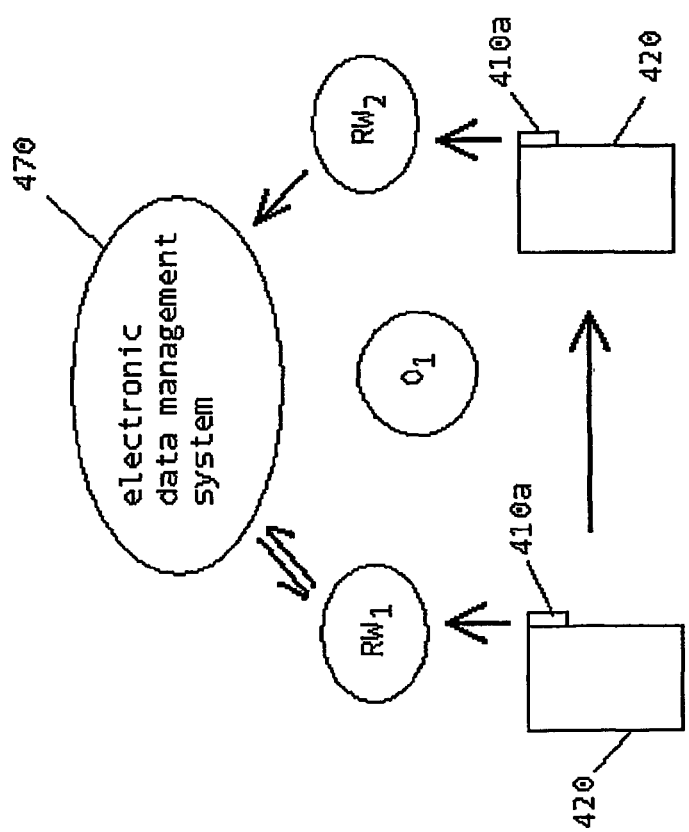
Figure 5D:
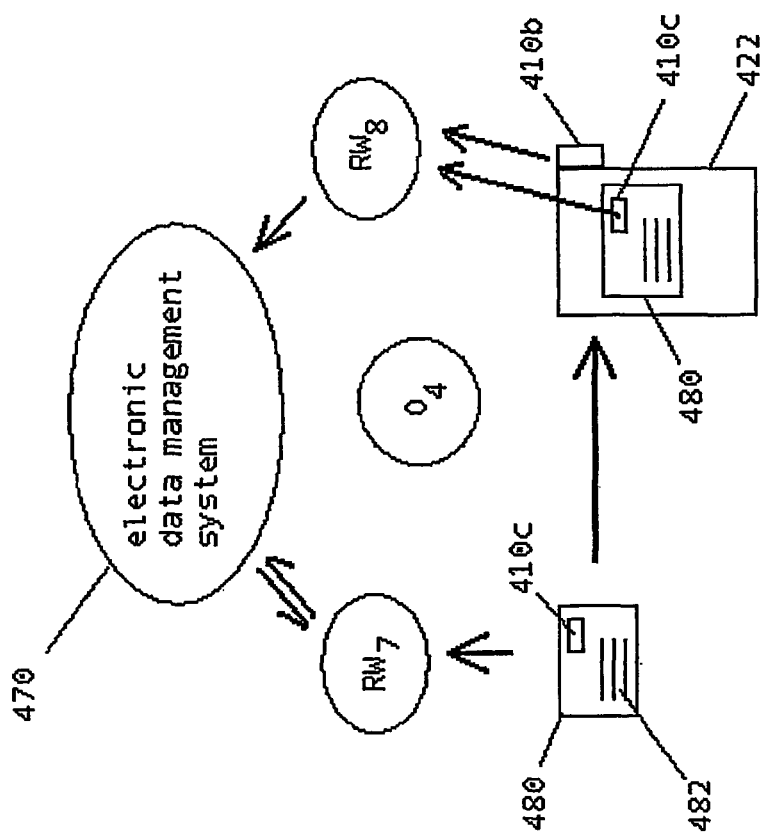
Figure 5C:
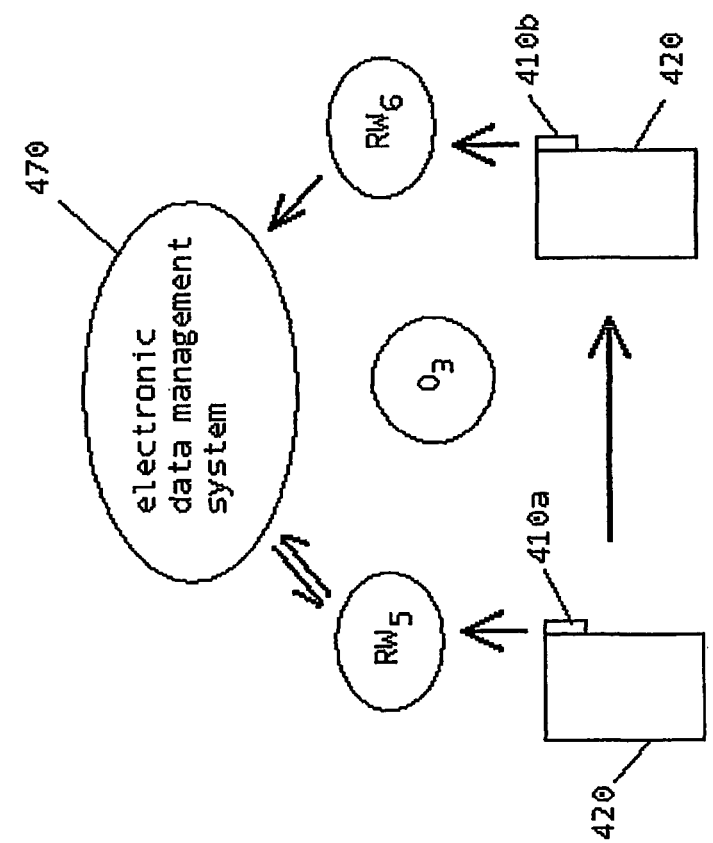

A first container 420, containing an investigator drug, is selected O1 by reading tag 410a attached thereto e.g. by means of a label 8 as described above by ReaderWriter RW1 in response to a signal from the relational database or electronic data management system 470 (FIG. 5a). The nature and quantity of the investigator drug is stored on the relational database or electronic data management system 470 (filling of the container 420 with this drug, and checking for compliance that this has been correctly done may have been carried out previously, and this may have been recorded on tag 410a and the electronic database management system 470). A compliance data item is written to the data management system 470 by RW2 on the successful selection of the container. In FIG. 5b a second, empty container 422, bearing a different RFID tag 410b is selected O2 by ReaderWriter RW3 and a data compliance item written to the data management system 470 by ReaderWriter RW4. FIG. 5c shows a defined quantity of drug being transferred O3 from the first 420 container (following identification by ReaderWriter RW5) to the second 422 container and a data compliance item written RW6 to the system 470.

A label 480, having a unique RFID tag 410c attached thereto, is printed which may contain bar coded or textual information relating to the specific clinical trial study. ReaderWriter RW7 confirms printing of the label by writing a data compliance item to the electronic data management system 470. The label 480 is affixed O4 to the second container 422. Both tags 410b and 410c are read by RW8 to validate that the label 480 has been affixed to the correct container 422 and an appropriate data compliance item sent to the system 470.

Figure 5E:
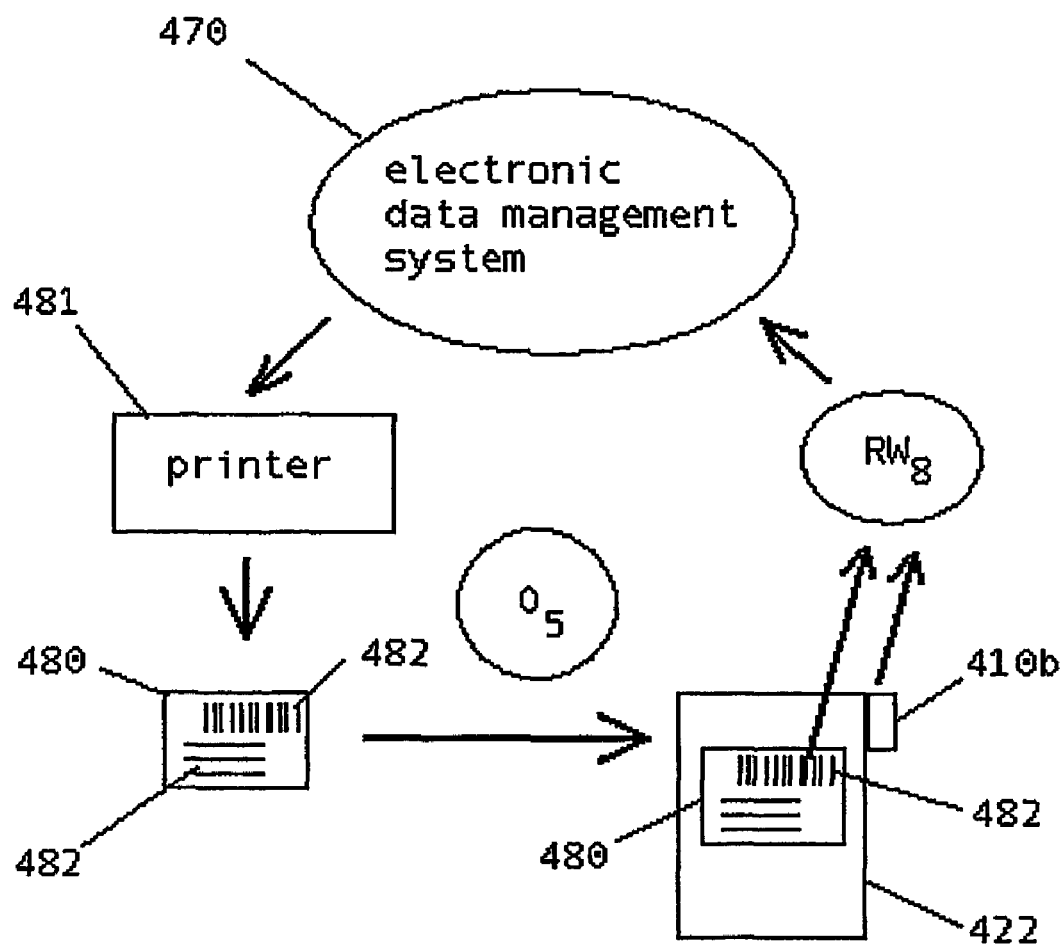

Alternatively or additionally, as shown in FIG. 5e the identity of the container 422 may be determined by the unique signature data item encoded on the tag 410b, and the identity of the container 422 and of the substance, e.g. drug, placebo or comparator, with which it is filled, e.g. in operation O3, may be stored in the database 470, together with associated labelling data such as a bar code and/or textual information 482 relating to the specific clinical trial study as mentioned above. A label 480 may then be generated, e.g. by a printer 481 driven by the database 470, and applied operation O5 to the container 422, the label 480 reproducing labelling data associated in the database 470 with the identified container 422. The label 480 may then be read, e.g. by reader writer RW8 reading a bar code 482 printed on label 480, and as a compliance check the read matter may be checked against the identity of container 422 as read from tag 410b stored in database 470 to validate that the correct label 480 has been applied.

The labelled container 422 may then be subjected to further operations, compliance with the associated compliance standard of which may be checked by the method of the present invention, analogously to those exemplified herein.

Figure 6:
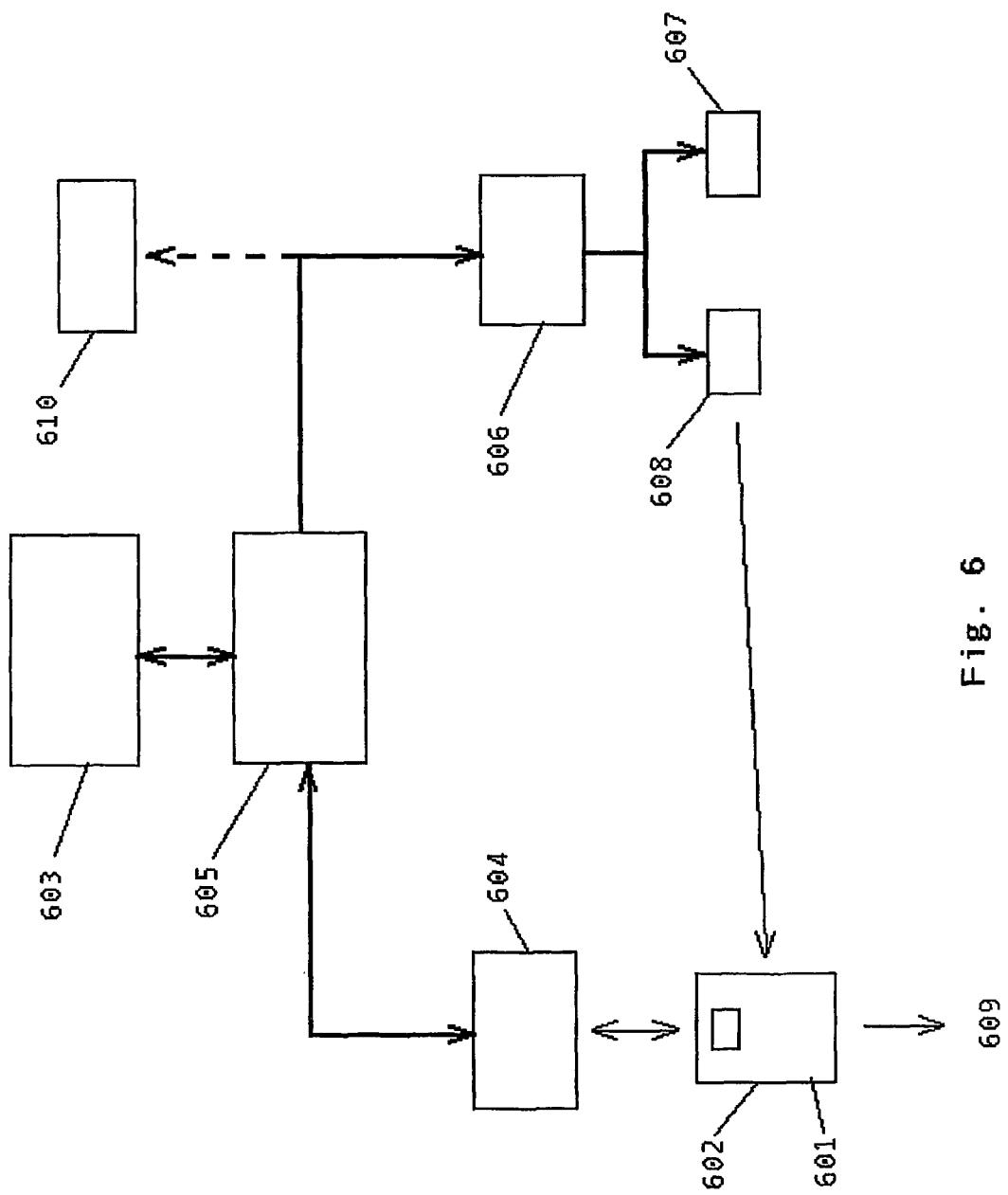
FIG. 6 illustrates a further application of the method of this invention.

Referring to FIG. 6 a further method of the invention is illustrated. A selected container 601 containing a drug substance for use in a clinical trial, having a unique signature data item encoded on a tag 602 mounted thereon, has been dispatched from a source 603 such as the clinical trials supply department of a pharmaceutical company, and received at a remote site being a clinic. The identity of the container 601 is read by a reader 604, for example the tag 602 may include an RFID which can be read by an RFID reader 604. The reader 604 is connected to a remote device 605, for example a desktop PC, laptop computer or PDA. The device 605 is electronically connected to the source 603 by a suitable data transmission link such as a telephone line, the internet or other computing network (LAN, WAN etc.), and the device 605 confirms (as a compliance item) with the remote site 603, e.g. automatically with a device (not shown) at the source 603, that the correct container 601 has been received at the remote site. The remote site will normally have been informed in advance by the source site 603 that container 601 will be or has been dispatched to the remote site and an investigator at the remote site can confirm that the correct container 601 has been received.

On confirmation that the correct container 601 has been received the device 605 causes a label printer 606 to print a confirmation record 607 that the correct container 601 is being dispensed (this can be an electronic record), and to print out a JIT label 608 to be attached to container 601. The JIT label 608 may contain the text specific to the dispensing such as the directions for use text, an up to date expiry date, the investigator's details, date of dispensing, a bar code, etc. Information that this has been done may be communicated back to the source site 603 as a further compliance item.

The investigator at the remote site then applies the JIT label 608 to the container 601. After this the label 608 as applied to the container 601 may be scanned, e.g. by a bar code reader (not shown) reading a bar code printed on the label 608 by printer 606, and the result of the scan communicated to device 605 to confirm as a compliance item that the label has been applied. Information that this has been done may be communicated back to the source site 603 as a further compliance item.

The container 601 may then be dispensed to patient 609, and as a further compliance item the identity of the patient 609 may be entered into the device 605 and correlated with the identity of the container 601.

Information concerning the container 601, and of its dispensing to the patient 609, e.g. time, date, patient identity etc. may be stored on the device 605 and attached to the Case Record File 610 together with the confirmation record 607.

By means of the system illustrated in FIG. 6 the source site 603 may be informed that the container 601 has been labelled and dispensed and is no longer available. Also any changes to the status of the container (e.g. expired, withdrawn) may be automatically detected, e.g. via an electronic link with the source site 603 to prevent inappropriate containers 601 being used. Returned containers 601 can similarly be scanned and accounted for, and the investigator at the emote site can add compliance details e.g. container 601 empty etc. at this point.

The invention claimed is:

1. A method for automatically tracking compliance in a clinical trials process involving the operations of preparing a label comprising textual information, applying the label to the container, and performing one or more following operation relating to the container comprising:

providing a container having associated therewith an identifier comprising a radio frequency identifier comprising an antenna for transmitting or receiving radiofrequency energy, and an integrated circuit chip connecting with said antenna, said chip comprising a memory having a unique signature item written thereon;

providing an apparatus comprising: means for selecting said container by reading the unique signature data item on the memory, means for writing said unique signature data item to a relational database, means for preparing a label comprising textual information and applying the label to the container; means for checking that the correct label has been applied against a compliance standard and, following the successful completion of applying the label to the container, for writing an associated compliance data item to said relational database and to the memory of the identifier;

selecting the container by reading the unique signature data item on the memory;

associating the identifier with said container;

reading said unique signature data item to the relational database;

performing the operation of applying the label to the container;

checking the that the correct label has been applied to the container against a compliance standard;

following the successful application of the label to the container, writing an associated compliance data item to said relational database and to the memory of the identifier;

wherein the compliance data item includes an acknowledgement that the correct label has been applied to the container;

then further comprising performing one or more following operation selected from list consisting of: introducing the correct type and quantity of a drug substance for trial, placebo or comparison drug substance into the container; applying or removing a closure to or from the container: storing the container in a predetermined location and subsequently removing the container therefrom; storing the container under suitable environmental conditions: selecting the container and enclosing it in a secondary pack; dispatching the container to or receiving the container from a predetermined address; transmitting information relating to the container to a predetermined recipient and, receiving information relating to the container from a predetermined recipient;

checking the performance of each following operation against a compliance standard;

and following the successful completion of each said following operation, writing an associated compliance data item to the database and to the memory of the identifier.

2. A method according to claim 1 wherein the following operation comprises the selection of a container and introducing the correct type, and quantity of a drug substance for trial, placebo or comparison drug substance into the container; the associated compliance standard being checking that the correct type, and/or quantity of a drug substance for trial, placebo or comparison drug substance has been introduced into the container.

3. A method according to claim 1 wherein the following operation comprises applying or removing a closure to or from a container; the associated compliance standard being checking whether or not the cap is in place.

4. A method according to claim 1 wherein the following operation comprises storing a container in a predetermined location and subsequently removing the container therefrom; the associated compliance standard being confirming that the correct container is at the correct location.

5. A method according to claim 1 wherein the first or further operation comprises storing a container or substance under suitable environmental conditions; the associated compliance standard being to ensure that suitable environmental conditions have been followed.

6. A method according to claim 1 wherein the following operation comprises selecting a container and enclosing it in a secondary pack; the associated compliance standard being checking that the correct container has been enclosed within the correct secondary pack.

7. A method according to claim 1 wherein the following operation comprises dispatching to or receiving a container at a predetermined address; the associated compliance standard being checking that the address is correct and/or that the correct container has arrived at the correct address.

8. A method according to claim 1 wherein the following operation comprises
transmitting to a predetermined recipient, and receiving information relating to the container by a predetermined recipient; the associated compliance standard being ensuring that the correct information is sent to and received by the correct recipient.

9. A method according to claim 1 wherein the unique signature data item comprises a unique machine readable number or code.

10. A method according to claim 1 wherein the method comprises reading the associated compliance data item and acknowledging confirmation of the reading prior to performing further operations relating to the container.

11. A method according to claim 1 wherein the method additionally comprises reading at least one compliance data item in the identifier memory prior to performing any following operation relating to the container.

12. A method according to claim 1 involving checking at least one compliance data item stored on the memory of the identifier or on the relational database against a defined criterion stored on the relational database.

13. A method according to claim 1 comprising a final reading step involving reading all compliance data items on the relational database and/or the identifier memory subsequent to the completion of the clinical trial operations.

14. A method according to claim 1 wherein the compliance data item comprises an operation or list of operations which must be carried out for full compliance to be registered and the subsequent checking involves ticking off the compliance data item, by writing to the database or identifier memory, associated with any operation once it has been completed.

15. A method according to claim 1 wherein a positive compliance data item for each operation is written to the database following the completion thereof.

16. A method according to claim 1 wherein the label comprises textual information and also an identifier comprising a unique signature data item, and confirming that the correct label is attached to the container is done by reading the unique signature data items attached to both the container and the label.

17. A method according to claim 1, wherein the identity of the container is determined by the unique signature data item encoded on a tag thereon, and the identity of the container and of a substance with which it is filled is stored in the relational database together with associated labelling data, a label is then generated and applied to the container, the label reproducing labelling data associated in the database with the identified container, the label is then read, and as a compliance check the read matter is checked against the identity of the container to validate that the correct label has been applied.

* * * * *